US006346386B1

(12) United States Patent
Elenitoba-Johnson (10) Patent No.: US 6,346,386 B1
(45) Date of Patent: Feb. 12, 2002

(54) METHOD OF SOLUTION-BASED SCANNING FOR ALTERATIONS IN A DNA SEGMENT USING A DOUBLE-STRANDED DNA BINDING DYE AND FLUORESCENCE MELTING PROFILES

(75) Inventor: Kojo S. J. Elenitoba-Johnson, Salt Lake City, UT (US)

(73) Assignee: ARUP Instiue, Salt Lake City, UT (US)

( * ) Notice: Subject to any disclaimer, the term of this patent is extended or adjusted under 35 U.S.C. 154(b) by 0 days.

(21) Appl. No.: 09/677,045

(22) Filed: Sep. 29, 2000

(51) Int. Cl.⁷ .......................... C12Q 1/68; C12P 19/34; G01N 33/00
(52) U.S. Cl. ............................ 435/6; 435/91.2; 436/94
(58) Field of Search ...................... 435/6, 91.2; 436/94

(56) References Cited

U.S. PATENT DOCUMENTS 6,174,670 B1 * 1/2001 Wittwer et al. ................ 435/6

OTHER PUBLICATIONS

Bohling et al (Laboratory Investigation (1999) 79(3): 337–345).*
Guldberg et al. (Biotechniques (1994) 16(5): 786–87).*
Carl T. Wittwer et al.; Continuous Fluorescence Monitoring of Rapid Cycle DNA Amplification; BioTechniques, vol. 22, No. 1 (1997); pp. 130–138.
Roger M. Wartell et al.; Detecting single base substitutions, mismatches and bulges in DNA by temperature gradient get electrophoresis and related methods; Journal of Chromatography A, 806 (1998); pp. 169–185.
Elaine Lyon et al.; Detection and Identification of Base Alterations Within the Region of Factor V Leiden by Fluorescent Melting Curves; Molecular Diagnosis, vol. 3, No. 4 (1998); pp. 203–210.
S. G. Fischer et al.; DNA fragments differing by single base–pair substitutions are separated in denaturing gradient gels: Correspondence with melting theory; Proc. Natl. Acad. Sci. USA, vol. 80 (Mar. 1983); pp. 1579–1583.
Sandra D. Bohling et al.; Fluorescence Melting Curve Analysis for the Detection of the bcl–1/JH translocation in Mantle Cell Lymphoma; Laboratory Investigation, vol. 79, No. 3, (Mar. 1999); pp. 337–345.
C.T. Wittwer et al.; The Light Cycler™: A Microvolume Multisample Fluorimeter with Rapid Temperature Control; BioTechniques, vol. 22, No. 1 (Jan. 1997); pp. 176–181.

Søren Germer et al.; Single–Tube Genotyping without Oligonucleotide Probes; Genome Research, (1999); pp. 72–78.
Sandra D. Bohling et al.; Rapid Simultaneous Amplification and Detection of the MBR/JH Chromosomal Translocation by Fluorescence Melting Curve Analysis; American Journal of Pathology, vol. 154, No. 1, (Jan. 1999); pp. 97–103.
Leonard S. Lerman et al.; Computational Simulation of DNA Melting and Its Application to Denaturing Gradient Gel Electrophoresis; Methods in Enzymology, vol. 155, (1987); pp. 482–501.
Russell Higuchi et al., Kinetic PCR Analysis: Real–time Monitoring of DNA Amplification Reactions; Bio/Technology, vol. 11 (Sep. 1993); pp. 1026–1030.
Val C. Sheffield et al.; Attachment of a 40–base–pair G+ C–rich sequence (GC–clamp) to genomic DNA fragments by the polymerase chain reaction results in improved detection of single–base changes; Proc. Natl. Sci. USA, vol. 86 (Jan. 1989); pp. 232–236.

* cited by examiner

Primary Examiner—Kenneth R. Horlick
Assistant Examiner—Alexander H. Spiegler
(74) Attorney, Agent, or Firm—Madson & Metcalf (57) ABSTRACT

A method for determining whether a DNA sequence is identical to a wild-type sequence is presented. A GC-rich DNA segment is attached to a DNA segment of interest. With the GC-clamp attached, the DNA segment of interest has two melting domains, a higher domain associated with the GC-clamp and a lower domain associated with the DNA segment of interest. The DNA segment of interest is labeled with a fluorescent label such as a double-stranded DNA binding dye and mixed with a denaturant. The mixture of denaturant and fluorescently labeled DNA is heated. Fluorescence is monitored to determine the melting point of the DNA segment of interest. The melting temperature of the DNA segment of interest is compared to the melting point of the wild-type sequence. A difference in melting temperatures of the DNA sequence and the wild-type sequence indicates an alteration in the DNA sequence. In a presently preferred embodiment, some homozygous mutations may be better detected by combining approximately equal parts of the DNA segment of interest with equal parts of the wild-type sequence to create a heteroduplex. The heteroduplex is fluorescently labeled and mixed with a denaturant. The mixture is heated while monitoring fluorescence to determine the melting point of the heteroduplex. A difference in melting temperatures of the heteroduplex and the wild-type sequence indicates an alteration in the DNA sequence.

26 Claims, 5 Drawing Sheets

METHOD OF SOLUTION-BASED SCANNING FOR ALTERATIONS IN A DNA SEGMENT USING A DOUBLE-STRANDED DNA BINDING DYE AND FLUORESCENCE MELTING PROFILES

BACKGROUND

1. The Field of the Invention

This invention relates to a method of identifying sequence alterations in a DNA fragment. More particularly the invention relates to a solution-based method of scanning for single base pair substitutions using fluorescence melting profiles and a double-stranded DNA binding dye.

2. Technical Background

Many human diseases and disorders are associated with genetic alterations. Many diseases can be attributed to a change or a mutation in a single gene. The diseases causes by genetic mutations may be diagnosed based on detection of a mutation within the genome of an individual. With early detection and the proper diagnosis, many of these disease may be treated. However, many of the currently available methods of detection are costly and labor intensive. Because of the labor involved the methods are subject to human error and run the risk of false results.

Several types of mutations can occur in DNA. A point mutation occurs when a single base is changed to one of the three other bases. A deletion occurs where one or more bases are deleted from a gene. An insertion occurs where new bases are inserted at a particular point in a nucleic acid sequence adding additional length to the sequence.

Large insertions or deletions can be readily detected within a DNA sample. Because of the small degree of molecular change, the point mutation is the most difficult type of mutation to screen for and detect. However, a number of diseases including some types of cancer are known to be caused by point mutations.

Methods that permit the detection of single base changes in specific regions of the genome have enjoyed tremendous utility in the field of genetics by facilitating genetic linkage analysis and the identification of mutations with specific disease associations, including those involved in the development and evolution of neoplasia. R. Wallace et al., *Science* 249:181–6 (1990); R. M. Cawthon et al., *Cell* 62:193–201 (1990); R. A. Flavell et al., *Cell* 15:25–41 (1978); A. P. Feinberg et al., *Science* 220:1175–1177 (1983); J. L. Bos et al., *Nature* 327:293–297 (1987); Hollstein et al., *Science* 253:49–53 (1991).

Single base alterations have been detected using a variety of methods. Some methods rely on the abolition or creation of novel restriction enzyme sites for example, restriction fragment length polymorphism analysis. Other methods use the polymerase chain reaction (PCR) and subsequent distinction of base mismatches by oligonucleotide hybridization. Single base changes have also been detected by the differences in the conformational or melting temperature characteristics of the mutated and wild-type sequences for example, single strand conformation polymorphism analysis and denaturation gradient gel electrophoresis. A. R. Wyman & R. White, *Proc Natl Acad Sci USA* 77:6754–6758 (1980); K. Mullis et al., *Cold Spring Harb Symp Quant Biol* 51:263–273 (1986); R. K. Saiki et al., *Science* 239:487–91 (1988); A. Neri et al., *Proc Natl Acad Sci USA* 85:9268–9272 (1988); M. Orita et al., *Proc Natl Acad Sci USA* 86:2766–70 (1989). All of these methods require multiple steps including gel electrophoretic separation and/or radioisotopic detection of the sequence variants. The use of radioisotopes creates safety concerns that increase the cost and limit the utility of these methods.

Recently, fluorescence-based technologies have been used for the detection of specific nucleic acid sequences. R. Higuchi et al., *Biotechnology (N Y)* 11:1026–30 (1993). These assays have typically exploited one of several fluorescence chemistries. C. T. Wittwer et al., *Biotechniques* 22:130–8 (1997). Some of these assays are non-specific methods and incorporate a double stranded DNA (dsDNA) binding dye such as SYBR® Green I into the amplification reaction. The specificity of product detection is entirely dependent on the inherent specificity of the amplification conditions. Subtle changes such as point mutations are difficult to detect using non-specific dsDNA binding dyes.

Other fluorescence-based assays are sequence-specific. These methods are probe-based and incorporate oligonucleotides that hybridize to a sequence within the amplified sample sequence. This method provides an additional parameter for verification of product identity. The specificity of the hybridization interaction has been further exploited for the identification of single nucleotide polymorphisms by virtue of the fact that the single base mismatches within the hybridization probe to DNA target hybrids exhibit lower melting temperatures than perfectly complementary strands. However, the detection of single base changes using probe-based methods is limited to very short segments of DNA of approximately 20 base pairs or less. The probe-based methods would require several probes in multiple separate reactions to scan a region of more than 100 bases. The cost of such probe-based assays is relatively high. Thus, the probe-based methods are unsuitable for mutational scanning of larger regions of DNA.

Unstacking of long helical DNA fragments has been shown in denaturing gel-based systems to occur in a succession of segments or discrete cooperative units referred to as domains. The melting temperatures (Tms) of these domains are principally determined by the base composition and precise DNA sequence. Single base differences in otherwise homologous DNA fragments can be discriminated provided that the differences are located within the lowest melting domain, and this domain is clearly separated from the onset of duplex to single strands dissociation. Both of these conditions can be satisfactorily achieved by the attachment of a higher melting section or a GC-rich sequence to the DNA fragment of interest, thus rendering the detection of virtually all single base changes possible. These principles have been exploited in such gel-based approaches as denaturation gradient gel electrophoresis and related methods. However, the gel-based systems require a significant amount of time, and are not readily adaptable to automation.

In light of the foregoing, it would be a significant advancement in the art to provide a solution-based method for detecting changes in a DNA sequence capable of screening DNA segments of greater than 20 base pairs. It would be an additional advancement if the method were capable of distinguishing even subtle single base changes from the wild-type. It would be an additional advancement if the method used a double-stranded DNA binding dye for detecting the mutation. It would be an additional advancement if the method were rapid and not labor intensive. It would be a further advancement if the method produced accurate and reproducible results. It would be an additional advancement if the method were adaptable to automation.

Such a method is disclosed herein.

BRIEF SUMMARY OF THE INVENTION

The present invention relates to a solution-based method for determining whether a DNA sequence is identical to a wild-type sequence. The alteration may be a point mutation such as a transversion or transition or other mutation such as an insertion or deletion. The method uses a dsDNA binding dye and fluorescent melting profiles to detect a mutation within a DNA segment of interest.

In a presently preferred embodiment, a sample of DNA suspected of containing a mutation is obtained. The sequence to be analyzed for the presence of an alteration is amplified to obtain an adequate amount of the sequence. A GC-rich segment is attached to the 5' end of the sequence of interest. This GC-clamp creates two melting domains, a higher domain associated with the GC-clamp and a lower domain associated with the DNA segment of interest. The GC-clamp may be of any length or sequence that confers a significantly higher melting temperature than that estimated for the sequence of interest.

In a presently preferred embodiment of the invention, a double stranded DNA (dsDNA) binding dye such as SYBR® Green I (Molecular Probes, Eugene, Oreg.), ethidium bromide, or YO-PRO-I® (Molecular Probes, Eugene, Oreg.) is included in an amplification reaction. The dsDNA binding dye attaches to the DNA as double-stranded amplicons are formed. The dye will continue to bind the DNA segment so long as the DNA remains double-stranded. Thus, the denaturation of the dsDNA will be observed as a significant reduction in fluorescence.

In one presently preferred embodiment of the invention, a sequence alteration may be detected by slowly heating the fluorescently labeled, GC-clamped DNA amplicon in the presence of a constant concentration of a denaturant. The mixture of the DNA segment of interest and denaturant is heated from below the melting temperature of the DNA segment of interest to above the melting temperature of the GC-clamp. In a presently preferred embodiment, the mixture is heated from about 33° C. to about 95° C. In a presently preferred embodiment of the invention, the mixture is heated at a rate less than 0.5° C./second. Preferably, the mixture is heated at a ramp rate of between about 0.01° C./second and about 0.1° C./second. More preferably, the rate of heating is about 0.02° C./second.

The fluorescence of the reaction mixture is monitored to determine the melting temperature of the segment of interest. Because the fluorescent label dissociates from the DNA as the DNA is melted, the melting point is seen as a significant reduction in fluorescence. In this manner, a mutation may be detected by comparing the melting point of a test DNA segment of interest to the melting point of the wild-type sequence. A difference in melting temperatures may indicate a mutation in the test DNA segment of interest.

The denaturant may be selected from a variety of denaturants such as urea. It is presently preferred that urea be used at a concentration of about 13.3M.

When a DNA sample contains a homozygous alteration in a sequence of interest, the melting temperature of the DNA sample, may be indistinguishable from that of a sample containing only wild-type sequence. This is especially true for point mutations such as transitions where the thermodynamic stability of the mutant and the wild-type sequence differ only very slightly. The method of the present invention may be adapted to detect such a mutation.

In a presently preferred embodiment, a polymorphism may be detected by creating an artificial heterozygote. This is accomplished by obtaining a sample of the DNA segment of interest. An approximately equal amount of the wild-type sequence is mixed with the sample sequence. The dsDNA dye generated melting temperature of the sample DNA:wild-type heteroduplex may then be compared to the melting temperature of the wild-type DNA to determine if the sample DNA contains one or more alterations.

The mixture is then amplified by PCR. The cyclical denaturation and renaturation of jointly amplifying the DNA sample and the wild-type sequence with PCR creates heteroduplexes. The heteroduplex is then mixed with a denaturant and slowly heated as described above. As the heteroduplex melts, the dsDNA dye dissociates from the DNA and a reduction in fluorescence is observed. The heteroduplex will exhibit two melting peaks in the lower melting domain or a broad transition in the lower melting domain. This is attributable to the presence of wild-type:wild-type, mutant:mutant, and mutant:wild-type duplexes in the reaction mixture. Often, the preparation of an artificial heterozygote is not necessary as the mutation that is being screened for is heterozygous in its natural state.

In summary, a solution-based method for determining whether a DNA sequence is identical to a wild-type sequence comprises coupling a GC-rich DNA segment to a DNA sample containing at least one copy of the DNA segment. The DNA sample in question is subjected to thermal cycling amplification which includes a dsDNA binding dye, and the reaction products are mixed with a denaturant and heated while monitoring fluorescence to determine the melting point of the amplicon. Germline heterozygous mutations form heteroduplexes with wild-type sequences, and this complex exhibits a lower melting temperature than wild-type homoduplexes. Homozygous mutations may be detected by combining approximately equal parts of the DNA sample with approximately equal parts of the wild-type sequence to create a heteroduplex. The double-stranded DNA bound heteroduplex is mixed with a denaturant and heated. A difference in melting temperatures of the DNA sample or the heteroduplex and the wild-type sequence indicates an alteration in the DNA sequence. This solution-based method is capable of reproducibly screening DNA segments greater than about 20 base pairs for alterations as small as a single base change. In the present embodiment, the region of interrogation is the entire length of a 104 bp DNA segment. The method is relatively rapid, requiring only about 40 minutes of post-amplification analysis, and is adaptable to automation.

These and other advantages of the present invention will become apparent upon reference to the accompanying drawings and graphs and upon reading the following detailed to description and appended claims.

BRIEF DESCRIPTION OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

FIGS. 5A–5C are a graphs illustrating mutational analysis by slow temperature ramping and chemical denaturation assessment of homozygous N-RAS codon 61 mutations. In FIG. 5A, the homozygous CAA→AAA transversion is indicated by the solid line. The dashed line indicates the wild-type sequence. The line with circles indicates the "$H_2O$" control.

DETAILED DESCRIPTION OF THE INVENTION

The present invention relates to a solution-based fluorescence method which is capable of determining whether a DNA sample is identical to a wild-type sequence. The method is sensitive enough to detect a change of a single base pair in a relatively large DNA fragment. In a preferred embodiment of the invention a double-stranded DNA binding dye is used to interrogate a region of more than 100 nucleotides. The method entails fluorescence monitoring of the melting temperatures of GC-clamped amplicons. The GC-clamped amplicons are subjected to gradual and progressive thermal denaturation in the presence of a constant concentration of a denaturant such as urea.

The method of the present invention can be used to detect a mutation as small as a single base substitution in a relatively large DNA fragment. An adequate amount of the sample DNA fragment to screen for a mutation can be obtained by amplification of the segment of interest. A wild-type fragment is used as a control for comparison to DNA segments of interest.

A segment of DNA with a high GC content may be incorporated into an oligonucleotide primer. This GC-rich segment or GC-clamp creates PCR amplicons with a high melting domain corresponding to the GC-clamp and a lower melting domain corresponding to the fragment of interest. A GC-clamp may be attached to a primer to generate PCR amplicons with a high melting domain juxtaposed to the DNA segment of interest. The GC-clamp may be of a variety of lengths so long as the GC-clamp provides a higher melting domain than the DNA segment of interest. A GC-clamp of about 40 bp typically provides a sufficiently high melting domain. The amplified fragment maintains a double-stranded configuration until it reaches its melting temperature (Tm). Because the disparity in Tms is most evident in a lower melting domain of a DNA fragment, it is possible to distinguish single base substitutions within the lower melting domain.

The method uses a fluorescent label to monitor the melting temperature of the DNA fragments. Such fluorescent labels include dsDNA binding dyes. Suitable dsDNA binding dyes include but are not limited to SYBR® Green I, ethidium bromide, and YO-PRO-I®. To create a method that is more readily adaptable to automation, it is presently preferred that the PCR amplicons are fluorescently labeled by including a double-stranded DNA binding dye in the amplification reaction. Double-stranded DNA binding dyes such as SYBR® Green I, ethidium bromide, and YO-PRO-I® are relatively inexpensive and easy to use. SYBR® Green I binds the minor groove of double-stranded DNA and exhibits an excitation maximum (497 nm) similar to that of fluorescein. YO-PRO-I® absorbs at 491 nm and emits at 509 nm. The fluorescence of double-stranded DNA binding dyes correlates with the quantity of double-stranded DNA in a sample and may, therefore, be monitored to determine the amount of double-stranded DNA present. For example, SYBR® Green I fluorescence has been monitored during PCR for quantitative PCR analysis in real time.

After PCR amplification, the samples are cooled to a temperature below the expected melting temperature of the DNA segment of interest. It is presently preferred that the sample be cooled to about 33° C., which is lower than the melting temperature of the double-stranded DNA. Once the sample is cooled to a temperature below the Tm, the sample is slowly heated in the presence of a denaturant to a temperature above the melting point of the GC-clamp. It one preferred embodiment the denaturant is urea and is used at a concentration of about 13.3 M. This slow heating or temperature ramping denatures the dsDNA and causes the fluorescent label to disassociate from the DNA. While the exact melting point of the GC-clamp depends on the length of the clamp sequence, it presently preferred that the temperature be slowly raised to a temperature between about 85° C. and about 95° C.

The temperature of the sample should be raised at a rate slow enough to distinguish between the Tms of the wild-type sequence and the fragment of interest. It is presently preferred that the temperature be increased at a rate of less than about 0.5° C./second to provide adequate distinction between melting temperatures of the fragment of interest and the wild-type fragment. A slower rate of temperature ramping of between about 0.1° C./second to about 0.01° C./second may allow for better distinction of melting temperatures and identification of a mutation in the sample of interest. More preferably a temperature ramping rate of about 0.02° C./second has been found to provide sufficient distinction between Tms and provide an overall rapid method of identifying mutant sequences.

As dsDNA is denatured, the binding of the fluorescent dsDNA binding dye is lost, and the denaturation of dsDNA is accompanied by a dramatic decrease in fluorescence. The melting temperature of a DNA sequence can be determined by monitoring and plotting this change in fluorescence. For easier visualization of the Tm, fluorescence melting peaks may be derived from the initial fluorescence versus temperature curves (F/T) by plotting the negative derivative of fluorescence over temperature versus temperature (−dF/dT versus T). Fluorescence signals should be collected at frequent intervals to monitor the fluorescence of the sample. It is presently preferred that the sample be monitored for fluorescence continuously during temperature ramping.

It has been found that samples containing DNA sequences with certain homozygous point mutations may be indistinguishable from the wild-type samples based solely on their respective melting temperatures. In order to distinguish such homozygous point mutations from the wild-type, an artificial heterozygote is created. In a presently preferred embodiment of the invention, a sample of DNA to be screened for a mutation is obtained. The DNA sample is mixed with the corresponding wild-type DNA fragment to create an artificial heterozygote. Preferably, the amount of wild-type DNA used is generally equal to the amount of the sample DNA. However, one of skill in the art will recognize that the sample DNA and wild-type DNA may be used in unequal concentrations without departing from the scope of the present invention.

The mixture of DNA sample and the wild-type DNA is amplified by polymerase chain reaction (PCR). The cyclical reiteration of denaturation and annealing during PCR generates heteroduplex molecules composed of wild-type and mutant DNA sequences in heterozygous samples.

Heterozygous mutations can be distinguished from the wild-type sequence by virtue of their variant melting profiles. The wild-type sequence displays only one melting transition in the lower melting domain. In contrast, the heterozygous mutants exhibit two melting sub-transitions within the lower melting domain. These results can be explained by the fact that heterozygous samples contain both the wild-type and mutant sequences which when annealed give rise to homoduplexes containing wild-type:wild-type and mutant:mutant fragments, and heteroduplexes consisting of mismatched mutant:wild-type hybrids. Because the Watson-Crick homoduplexes are more thermodynamically stable than the heteroduplexes, they exhibit higher Tms than the less stable heteroduplex mismatches. Thus the heterozygous mutants can be identified by the additional sub-transition with a lower Tm than is observed for the wild-type sample.

Figure 5A:
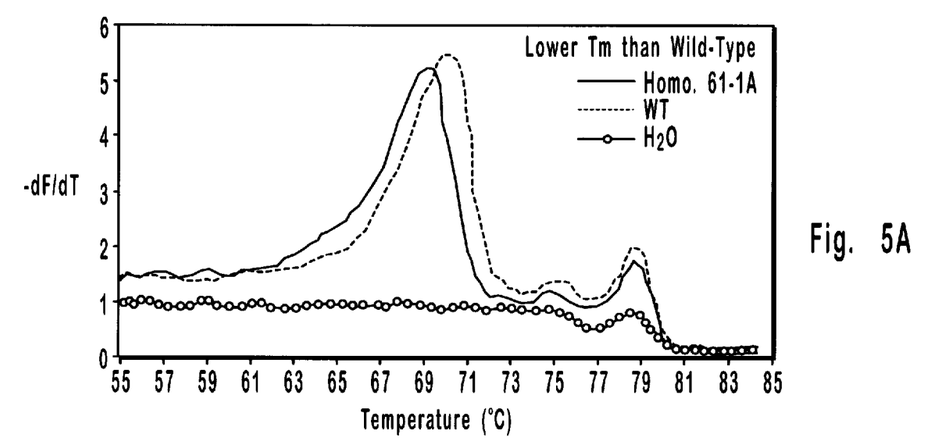
Figure 5B:
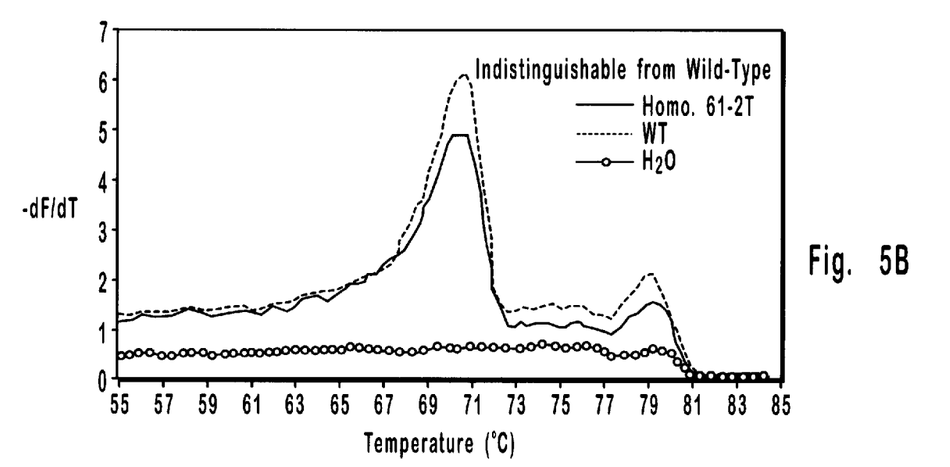
FIG. 5B is a graph illustrating assessment of the homozygous CAA→CTA transition of homozygous N-RAS codon 61. The dashed line indicates the wild-type sequence. The solid line indicates the homozygous mutant samples. The line with circles indicates the "$H_2O$" control.
Figure 5C:
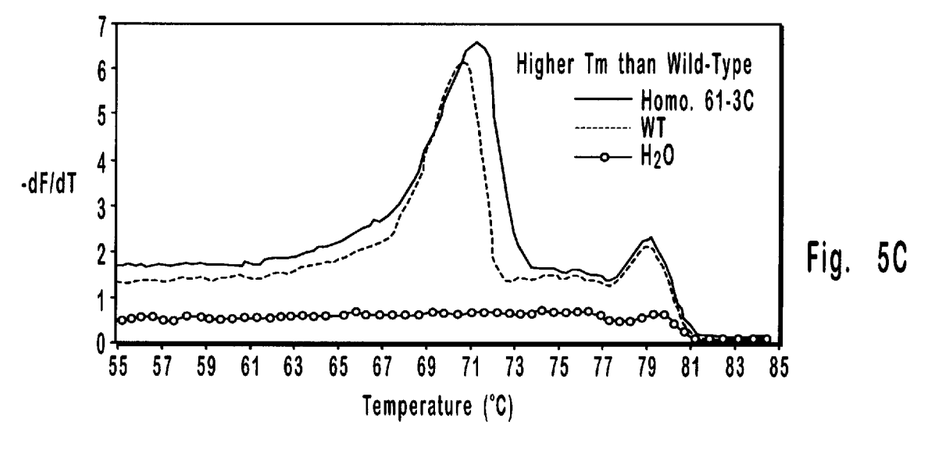
FIG. 5C is a graph illustrating assessment of the homozygous CAA→CAC transversion. The dashed line indicates the wild-type sequence. The solid line indicates the homozygous mutant samples. The line with circles indicates the "$H_2O$" control.

The method of the present invention identifies single base substitutions by the presence of two distinct melting sub-transitions within the lower melting domain, or by the presence of a single composite and broader melting transition with a lower Tm than observed for the wild-type sequence. The differences in the Tms of the wild-type homoduplexes and wild-type:mutant heteroduplexes have been found to range from 1.0 to 2.0° C., thus rendering both peaks distinguishable in most cases. The in vitro generated homozygous mutants are composed of Watson-Crick hybrids with subtle Tm differences from the wild-type samples. In most cases the differences were consistent with the canonical thermodynamic stabilities of the mutant hybrids relative to the wild-type sequence (FIG. 5). Nevertheless, the strategy of heteroduplex analysis performed by mixing homozygous mutants with wild-type DNA provided a sensitive means for the detection of all mutations evaluated.

This methodology is advantageous in that it is simple and rapid, requiring only about 40 minutes of post-amplification analysis for mutational screening to be completed. Furthermore, gel electrophoresis is not required, neither is there a need for radioactive, biotinylated, or fluorescently labeled oligonucleotide probes. While other solution-based fluorescent methodologies utilized for detection of point mutations are limited to short (~20 bp) segments, the current method is particularly applicable when the precise site of the mutation or polymorphism is unknown in advance, or spans a length of 100 nucleotides or more. Tm alterations comparable in magnitude to those observed for single base substitutions can be expected from single base pair insertions or deletions. The approach can be adapted to screening of DNA fragment of more than 200 base pairs. The present method expands the region of interrogation for detection of point mutations using fluorescence-based methods in solution and is amenable for automation and adaption to high-throughput systems.

All publications, patents, and patent applications cited herein are hereby incorporated by reference.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Predicted Melting Domains for the 104 bp Test DNA Fragment

Figure 1:
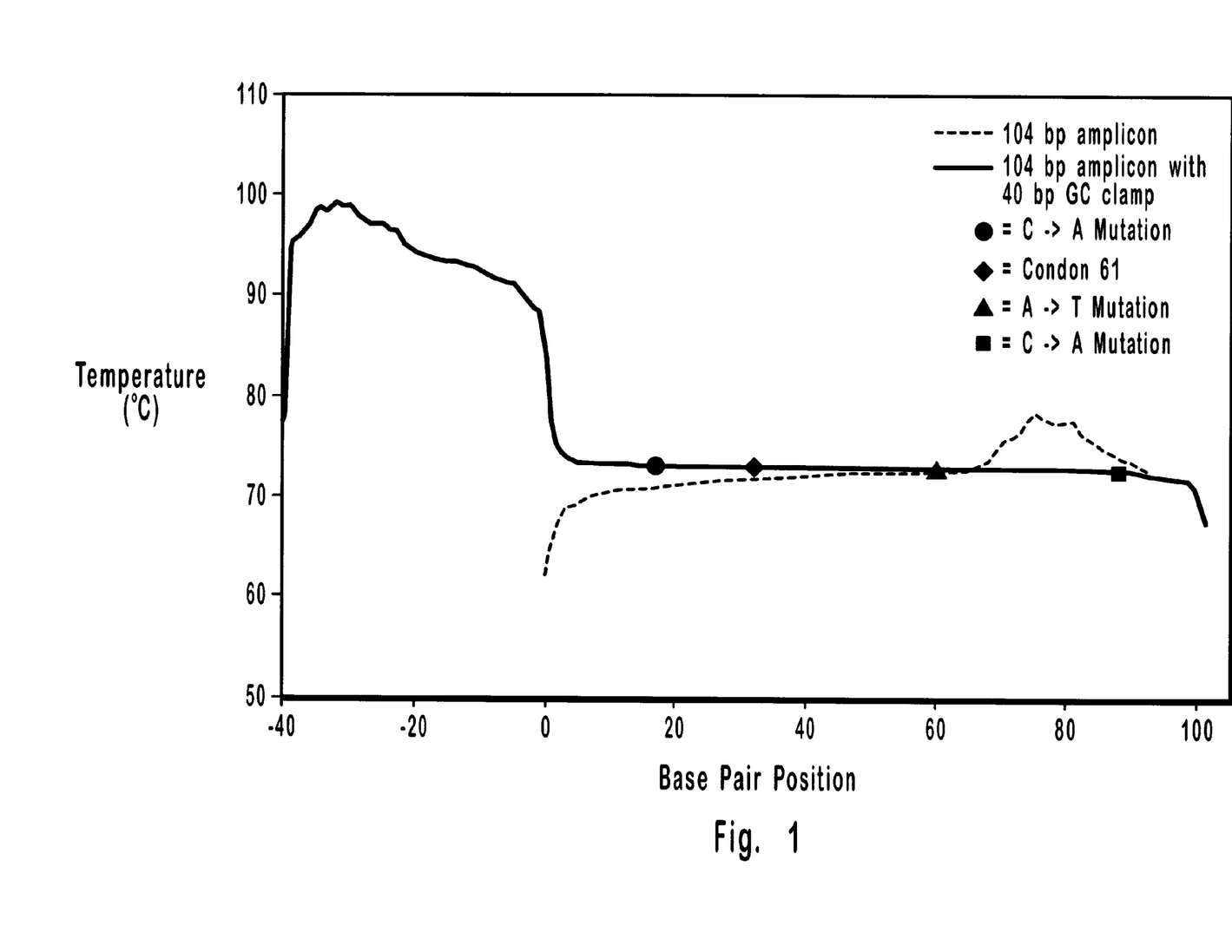
FIG. 1 is a graph illustrating predicted melting domains for the 104 bp N-RAS exon 2 amplicon. The dashed line represents the 104 bp N-RAS exon 2 fragment, and the solid line represents the 104 bp fragment with attached 40 bp GC-clamp at its 5' end (nucleotide #−40).

Computer algorithms have been used to predict the melting behavior of a DNA fragment based on its nucleotide sequence. L. S. Lerman & K. Silverstein, *Methods Enzymol* 155:482–501 (1987). Referring to FIG. 1, Tm is plotted against the nucleotide sequence in the predicted melting domain computational constructs. All DNA sequences were analyzed using the WINMELT DNA analysis program (MedProbe AS, Oslo, Norway). A 104 bp N-RAS exon 2 fragment (GenBank Accession #L00041, nucleotides #38 to 141) was the target of interest for assessment of the presence of single base substitutions. The dashed line represents the 104 bp N-RAS exon 2 fragment, and the solid line represents the 104 bp fragment with attached 40 bp GC-clamp at its 5' end (nucleotide #−40). The predicted melting profile of the 104 bp N-RAS exon 2 product exhibits 2 melting domains: a lower melting domain with a theoretical Tm of 72° C.

spanning nucleotides 1–67 and a higher melting domain with a Tm of 78° C. spanning nucleotides 68–104. Similar analysis was performed on the same N-RAS exon 2 fragment, but with a 40 bp GC-clamp attached to its 5' end. This product exhibited 2 distinct melting domains: a high-melting domain corresponding to the GC clamp (Tm=93° C.), and a low melting region (Tm=74° C.) corresponding to the 104 bp segment being assessed for the presence of single base changes. This renders the detection of point mutations possible throughout the length of the fragment of interest.

Example 2
Preparation of DNA Templates

DNA was extracted from peripheral blood lymphocytes of healthy individuals and human placenta. All samples were confirmed by sequencing to contain the wild-type N-RAS exon 2 sequence and utilized as wild-type controls.

Nine 104 bp DNA fragments were synthesized. Each fragment contained one of the possible base substitutions in codon 61 of the N-RAS gene by PCR site-directed mutagenesis. PCR amplifications were performed using 44 bp long mutagenic forward primers to incorporate the desired mutations. Primers were designed against the N-RAS exon 2 DNA sequence (GenBank accession #L00041) using Primer Designer for Windows (Scientific and Educational Software, State Line, Pa.). A Perkin Elmer 2400 thermal cycler (Perkin Elmer, Norwalk, Conn.) was used to perform the PCR amplifications consisting of 30 cycles of denaturation (94° C. for 60s), annealing (60° C. for 60s) and extension (72° C. for 60s). A final extension of 72° C. for 7 minutes was also included in the amplification protocol. The resulting amplification products were subjected to electrophoresis on ethidium bromide stained 1.5% agarose gels and the bands of appropriate size were excised and purified using Amicon DNA extraction columns (Millipore Corporation, Bedford Mass.). The presence of the desired mutations was confirmed by direct sequencing using the ABI PRISM 377 (Perkin Elmer Applied Biosystems, Calif.).

Three additional PCR products with single base substitutions at nucleotides #18 (C to A transversion), #61 (A to T transition), and #89 (C to A transversion) of the 104 bp N-RAS exon 2 amplicon were obtained (GenBank Accession #L00041; nucleotides 38 to 141). PCR amplifications were performed using a 25 bp long mutagenic forward primer, a 57 bp long mutagenic reverse primer and a 24 bp long mutagenic reverse primer, respectively (Table I). The PCR amplification, product purification, and DNA sequence confirmation were performed as described above.

TABLE I

Primers Utilized for synthesis of mutant N-RAS exon 2 templates

| Primer | Sequence | GenBank Acc.# | Paired with |
|---|---|---|---|
| Codon-56-1A | 5'-CCTGTTTGTTGGACATA<u>A</u>TGGATAC-3' (SEQ ID NO: 1) | L00041 | Exon2-R |
| Codon-61 | 5'-CCTGTTTGTTGGACATACTGGATACAGCTGGAXYZGAAGAGTAC-3' (SEQ ID NO: 2) | L00041 | Exon2-R |
| Codon-70-2T | 5'-GATGGCAAATACACAGAGGAAGCCTTCGCCTGTCCTCATGT<u>A</u>GGTCTCTCATGGC-3' (SEQ ID NO: 3) | L00041 | Exon2-F |
| Codon-80-3A | 5'-GATGGCAAATACACA<u>T</u>AGGAAGCC-3' (SEQ ID NO: 4) | L00041 | Exon2-F |

Underlined letters indicate position of base substitutions in codons 56, 70, and 80.
X, Y, and Z represent the nucleotide positions in codon 61 at which a base substitution was introduced into the primer. Only one base was substituted in each primer. The wild-type sequence in codon 61 is CAA. Thus, mutational insertions at position X were A, G, T; in position Y were C, G, T; and in position Z were C, G, T.

The heterozygous state for each mutation was simulated by mixing equivalent amounts of homozygous mutant DNA and wild-type genomic DNA. DNA from four cell lines harboring heterozygous mutations in codon 61 of N-RAS were also utilized as templates for PCR and fluorescence analysis during slow temperature ramping.

Example 3
PCR Amplification of N-RAS Sequences

Rapid cycle PCR amplification was performed in a microvolume fluorimeter (LIGHTCYCLER, Roche Molecular Biochemicals, Indianapolis, Ind.) (18) using a 20 bp forward primer (5'-CTT GTT TGT TGG ACA TAC TG-3') (SEQ ID NO: 5) and a 20 bp reverse primer (5'-GAT GGC AAA TAC ACA GAG GA-3') (SEQ ID NO: 7) specific for exon 2 of the N-RAS proto-oncogene. Briefly, a 100 ng aliquot of template DNA was amplified in a 20 μL reaction containing 1X PCR buffer (50 mM Tris [pH8.5], 3.0 mM MgCl$_2$, 500 μg/mL bovine serum albumin), four deoxynucleotide triphosphates (dNTPs) at 200 μmol/L each, 0.2 μmol/L of each primer, 10% DMSO (by volume) and 0.4 unit of Promega DNA polymerase with 11 ng/μL of TaqStart antibody (CloneTech, Palo Alto, Calif.). DNA amplification consisted of 45 cycles of denaturation at 94° C. for 0 seconds, annealing at 50° C. for 0 seconds and extension at 72° C. for 10 seconds. Each reaction included SYBR® Green I (1:30, 000 dilution, Molecular Probes, Eugene, Oreg.), which interacts with all dsDNA. In the LIGHTCYCLER, filtered excitation light (450 to 490 nm) from a blue light emitting diode is reflected from a 505 nm dichroic filter and focused on the capillary tip, thus interrogating the samples by paraxial epi-illumination. A portion of the excitation light is passed up the capillary tube by total internal reflection at the glass/air interface. Similarly, emitted light is passed down the capillary tube and exits out at the tip. The light is then filtered through a 520-560-nm interference filter and focused onto silicon photodiodes for detection. Fluorescence signals were obtained once in each cycle by sequential fluorescence monitoring of each tube at the end of extension.

The incorporation of a GC-clamp to an oligonucleotide primer affords the generation of PCR amplicons with a high melting domain corresponding to the GC-clamp and a lower melting domain corresponding to the fragment of interest. V.

C. Sheffield et al., *Proc Natl Acad Sci USA* 86:232–6 (1989). In order to create GC clamped amplicons, 40 bp clamps were attached to the forward primer to generate PCR amplicons with a high melting domain juxtaposed to the DNA segment of interest. The amplified fragment maintains a double-stranded configuration until it reaches its melting temperature. Fischer, S. G. & Lerman, L. S. (1983) *Proc Natl Acad Sci U S A* 80, 1579–83. Since the disparity in Tms is most evident in the lower melting domain of the fragment, it is possible to distinguish single base substitutions within the lower melting domain. Rapid cycle PCR amplification for synthesis of the GC-clamped amplicons was performed in a microvolume fluorimeter (LIGHTCYCLER, Roche Molecular, Indianapolis, Ind.) using a 40 bp GC-clamp attached to a 20 bp forward primer (5'-CGC CCG CCG CGC CCC GCG CCC GTC CCG CCG CCC CCG CCC GCC TGT TTG TTG GAC ATA CTG-3') (SEQ ID NO: 6) and a 20 bp reverse primer (5'-GAT GGC AAA TAC ACA GAG GA-3') (SEQ ID NO: 7) specific for exon 2 of the N-RAS proto-oncogene. The amplification conditions were as otherwise described for the non-GC clamped sequences.

Example 5
Mutational Scanning by Slow Temperature Ramping and Chemical Denaturation of GC-Clamped Amplicons After the above described amplification was completed, the amplicon was removed from the capillary tubes by reverse centrifugation. 10 μL of the PCR products were added to 10 μL of 26.6M urea and mixed vigorously to produce a final urea concentration of 13.3M. 10 μL of this amplicon/urea mixture were subjected to post-amplification fluorescence analysis during slow temperature ramping. The procedure entailed continuous acquisition of fluorescence during gradual temperature elevation from 33° C. to 85° C. at a ramp rate of 0.02° C./sec in the presence of a constant concentration of urea (13.3M). SYBR® Green I fluorescence signals were continuously monitored during post-amplification denaturation process. For easier visualization of the melting temperatures, the fluorescence melting curves (F versus T) were converted into fluorescence melting peaks by plotting the negative derivative of fluorescence over temperature versus temperature (–dF/dT versus T).

Figure 3A:
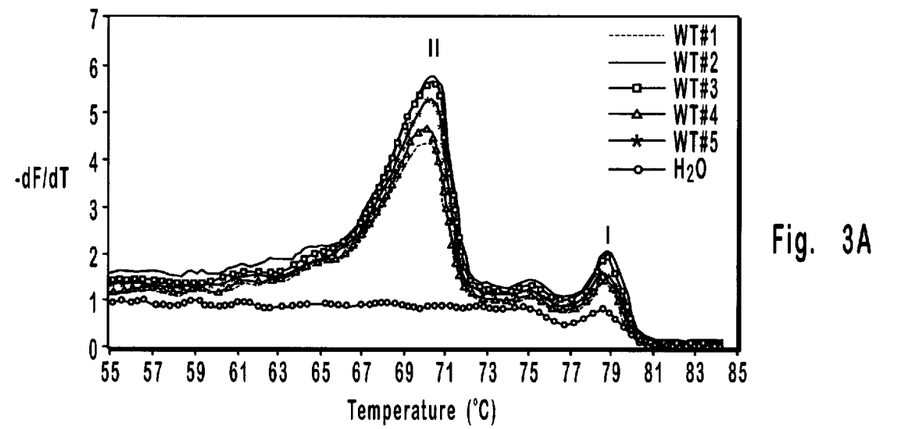
FIG. 3A is a graph illustrating the reproducibility of melting profiles generated using mutational scanning by slow temperature ramping and chemical denaturation. Melting peak (I) represents the 40 bp GC-clamp with a higher Tm (~79° C.). Melting peak (II) represents the 104 bp segment of interest. WT indicates wild-type replicates. The line with circles indicates the "$H_2O$" control.
Figure 3B:
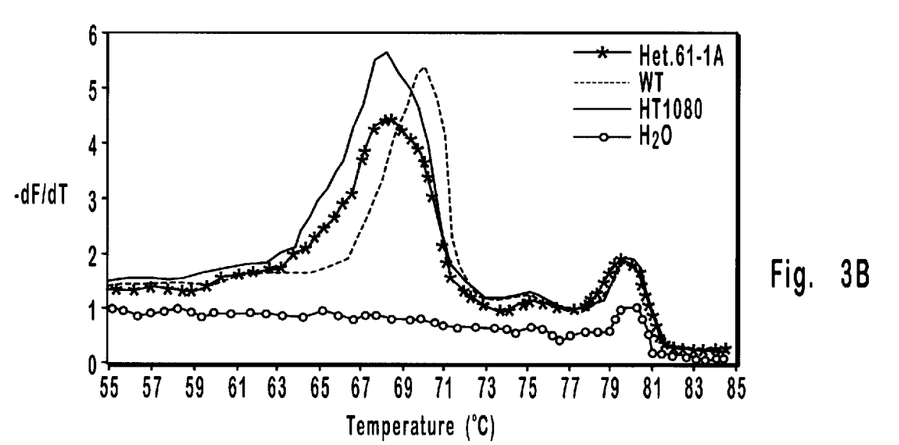
FIG. 3B is a graph illustrating mutational scanning by slow temperature ramping and chemical denaturation detection of heterozygous N-RAS codon 61 CAA→$\underline{A}$AA (Q61K) mutation. The HT1080 cell line (solid line) and a 50/50 mixture of the in vitro generated homozygous Q61K mutant and wild-type DNA (X-line) represent heterozygous mutants harboring the CAA→$\underline{A}$AA mutation (61-1A). The HT1080 cell line is indicated by a solid line. The dashed line indicates the wild-type sequence. The line with circles indicates the "$H_2O$" control.
Figure 3C:
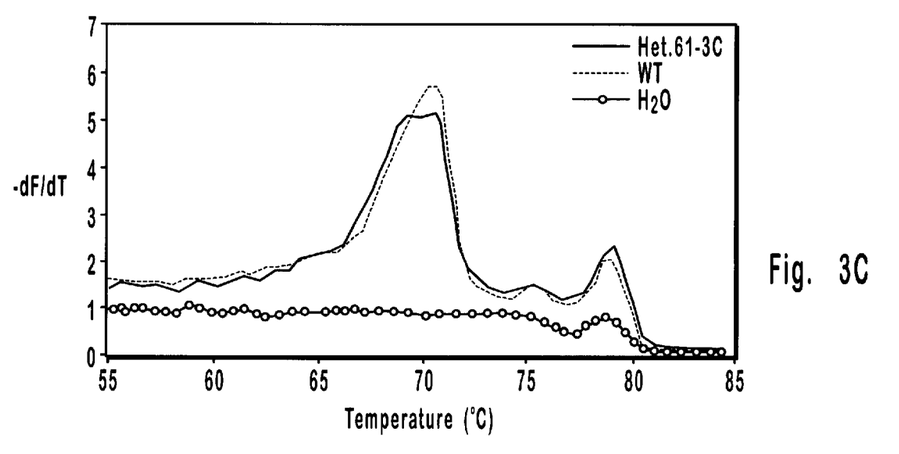
FIG. 3C is a graph showing detection of heterozygous N-RAS codon 61 CAA→CA$\underline{C}$ (Q61H) mutation. The dashed line indicates the wild-type sequence. The solid line indicates the heterozygous samples. The line with circles indicates the "$H_2O$" control.

Referring to FIG. 3, post amplification fluorescence analysis performed on GC-clamped amplicons derived from

TABLE II

Primers Utilized for amplification of N-RAS sequences

| Primer | Sequence | GenBank Acc.# | Paired with |
|---|---|---|---|
| Exon2-F | 5'-CCTGTTTGTTGGACATACTG-3' (SEQ ID NO: 5) | L00041 | Exto2-Rt, Exon2-R |
| Exon2F(GC) | 5'-*CCTGTTTGTTGGACATACTG-3' (SEQ ID NO: 6) | L00041 | Exon2-R |
| Exon2-R | 5'-GATGGCAAATACACAGAGGA-3' (SEQ ID NO: 7) | L00041 | Exon2F(GC), Exon2-F |
| Exon2-Ft† | 5'-*CCTGTTTGTTGGACA-3' (SEQ ID NO: 8) | L00041 | Exon2-R |
| Exon2-Rt‡ | 5'-*GATGGCAAATACA#3' (SEQ ID NO: 9) | L00041 | Exon2-F |

*Indicates position of GC-clamp
5'-CGCCCGCCGCGCCCCGCGCCCGTCCCGCCGCCCCGCCCG-3' (SEQ ID NO: 10).
†For amplification of codon 56 mutant sequences, a truncated forward primer containing the GC clamp was used.
‡For amplification of codon 80 mutant sequences, the reverse primer contained the GC clamp rather than the forward primer.

Example 4
Standard Fluorescence Melting Curve Analysis Without the GC-Clamp Does Not Permit Detection of Single Base Substitutions Throughout the Length of the Amplicon Post amplification melting curve analysis was performed using amplicons created from wild-type DNA sequences, in vitro generated homozygous mutant DNA, heterozygous cell line DNA and 50/50 mixtures of homozygous mutant and wild-type DNA mixtures (artificial heterozygotes). After PCR amplification, the samples were cooled to 33° C. at a rated of 20° C./sec, and then heated slowly at 0.1° C./second to 95° C. Fluorescence signals were collected continuously to monitor the SYBR® Green I fluorescence. For easier visualization of the melting temperatures, fluorescence melting peaks were derived from the initial fluorescence curves (fluorescence (F) versus temperature (T)) by plotting the negative derivative of fluorescence over temperature versus temperature (–dF/dT versus T).

Figure 2:
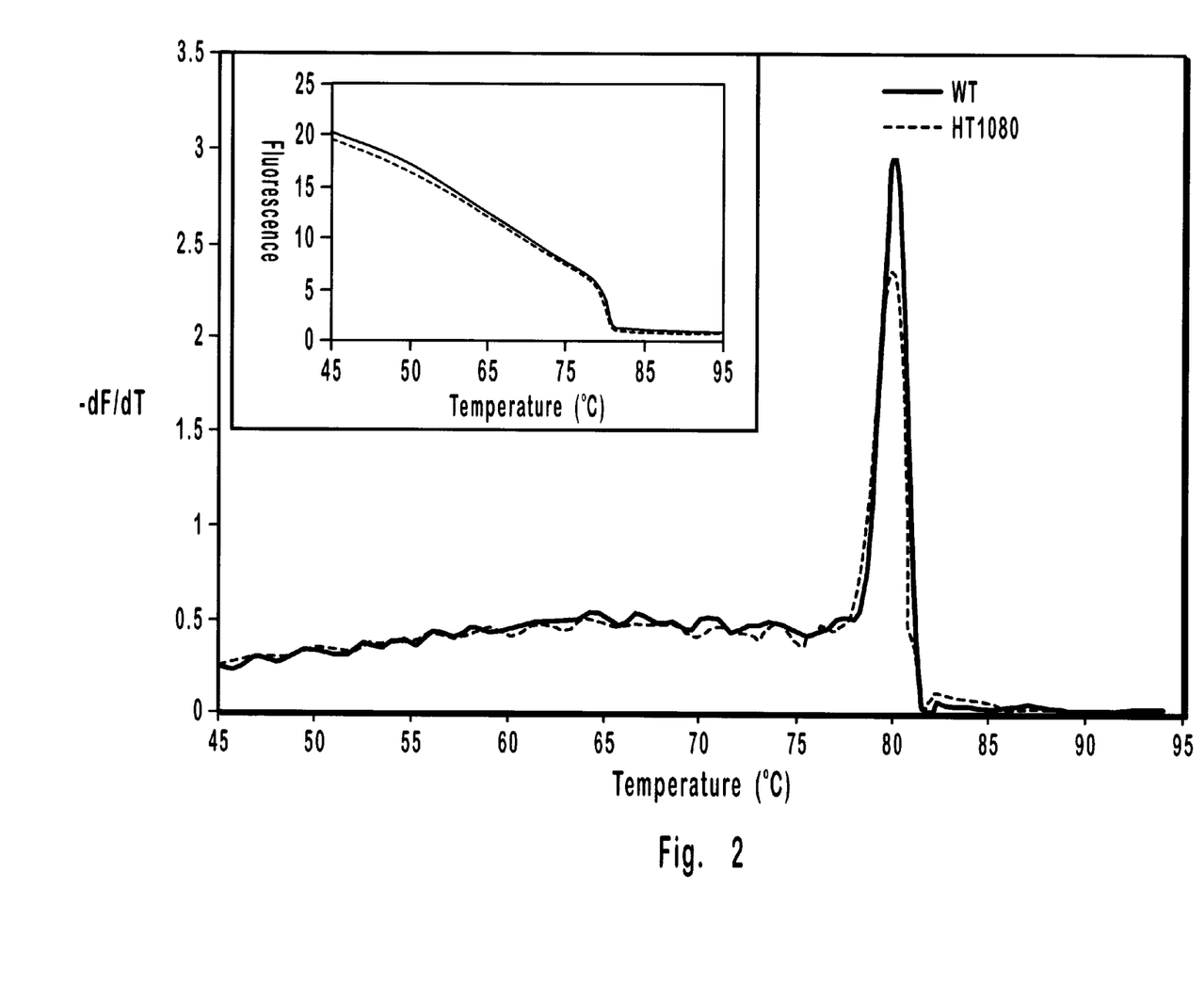
FIG. 2 is a graph illustrating the fluorescence melting curve analysis for the 104 N-RAS exon 2 amplicon. The solid line represents the melting profile of the 104 bp wild-type N-RAS exon 2 amplicon. The dashed line represents the profile of the same amplicon using the HT1080 cell line which harbors a heterozygous CAA→AAA transversion in codon 61. The inset is a graph of a fluorescence melting curve showing a superimposable sharp decline in fluorescence in both the wild-type and heterozygous mutant products demonstrating that both are indistinguishable by standard fluorescence melting curve analysis.

Referring to FIG. 2, the wild-type 104 bp N-RAS amplicon showed an abrupt decline in fluorescence (F) at 80° C. on the fluorescence versus temperature (T) curves. A corresponding melting peak was evident at 80° C. on the –dF/dT versus T plots. All of the cell line DNA samples harboring heterozygous N-RAS mutations, the artificial mixtures and the synthetic homozygous mutants yielded melting profiles indistinguishable from that obtained for the wild-type sequence.

the 104 bp segment encompassing codon 61 of the wild-type N-RAS gene showed two distinct melting domains for all products. Fluorescence (F) versus temperature (T) plots at both ramp rates revealed similar profiles consisting of a lower melting domain at 70° C. corresponding to the amplified 104 bp N-RAS exon 2 segment of interest, and a higher melting domain at 79° C. corresponding to the 40 bp GC clamp. Referring to FIG. 3A, the Tms of these two melting domains were better visualized by assessing the fluorescence melting peaks derived from the negative derivative of fluorescence over temperature (–dF/dT) versus temperature (T) plots. While the Tms of the two domains were distinct, the melting domains exhibited melting temperature transitions spanning 64–71° C. (DNA fragment of interest) or 78–80° C. (GC clamp).

Example 6
Mutational Scanning by Slow Temperature Ramping and Chemical Denaturation of GC-Clamped Amplicons of Heterozygous N-RAS Mutant DNA Artificial DNA targets composed of 50/50 mixtures of wild-type DNA and homozygous PCR mutants and the 4 cell lines previously determined to contain heterozygous N-RAS mutations in codon 61 were prepared. Referring to FIGS. 3B and 3C, a ramp rate of 0.02° C./second permitted adequate resolution of mutant from wild-type melting peaks in the heterozygous samples and thus was employed for the assessment of the mutations. All 9 heterozygous mutations in N-RAS codon 61 were distinguishable from the wild-type sequence, by virtue of their variant melting profiles. In contrast to the wild-type sequence which displayed only one melting transition in the lower melting domain, the heterozygous mutants exhibited two melting sub-transitions within the lower melting domains. The "$H_2O$" control shows fluorescence at levels below background.

These results can be explained by the fact that heterozygous samples contain both the wild-type and mutant sequences which when annealed give rise to homoduplexes containing wild-type:wild-type and mutant:mutant fragments, and heteroduplexes consisting of mismatched mutant:wild-type hybrids. Because the Watson-Crick homoduplexes are more thermodynamically stable than the heteroduplexes, they exhibit higher Tms than the less stable heteroduplex mismatches. Thus the heterozygous mutants were identifiable by the presence of additional subtransition with a lower Tm than was observed for the wild-type sample.

Example 7
Reproducibility of Results

FIG. 3A illustrates the reproducibility of melting profiles generated using mutational scanning by slow temperature ramping and chemical denaturation. The amplicons to be assessed are GC-clamped at one end and subjected to gradual temperature denaturation at the rate of 0.02° C./second in the presence of 13.3M urea. Quintuplicate analyses of the GC-clamped wild-type N-RAS exon 2 product reveals two major melting domains. Melting peak I represents the 40 bp GC clamp with a higher Tm (~79° C.). Melting peak II represents the 104 bp segment of interest. All 5 wild-type replicates show an identical melting profile with the same Tm in both melting domains. The "$H_2O$" control shows fluorescence at levels below background.

Example 8
Mutational Scanning by Slow Temperature Ramping and Chemical Denaturation Analysis of Artificially Induced Single Base Substitutions Analysis of artificially induced single base substitutions throughout the length of the 104 bp DNA sequence (within the lower melting domain of the GC-clamped amplicon) was also performed using artificial DNA targets composed of 50/50 mixtures of wild-type genomic DNA and homozygous PCR mutants. These mutants consisted of a C to A substitution at nucleotide #18 (codon 56), an A to T substitution at nucleotide #61 (codon 70), and a C to A substitution at nucleotide #89 (codon 80). Referring to FIG. 4, all of these heterozygous mutations were easily distinguished from the wild-type sequence by their variant melting profiles. One third of the heterozygous mutants exhibited one broad melting transition with a lower Tm than that of the wild-type sequence (FIG. 4A).

Figure 4A:
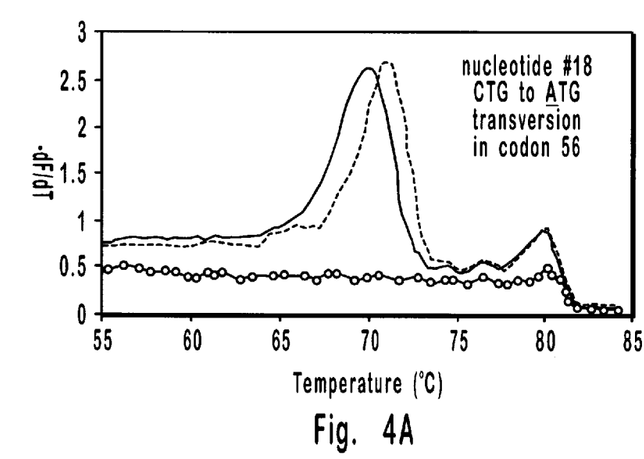
FIG. 4A is a graph showing detection of heterozygous N-RAS codon 56 CTG→ATG transversion. The dashed line indicates the wild-type sequence. The solid line indicates the heterozygous samples. The line with circles indicates the "$H_2O$" control.

Referring to FIG. 4A a detection of heterozygous N-RAS codon 56 CTG→ATG transversion is illustrated. An anomalous melting profile easily distinguishable from the wild-type profile is observed for the artificial heterozygous mutant. The "$H_2O$" control shows fluorescence at levels below background.

Figure 4B:
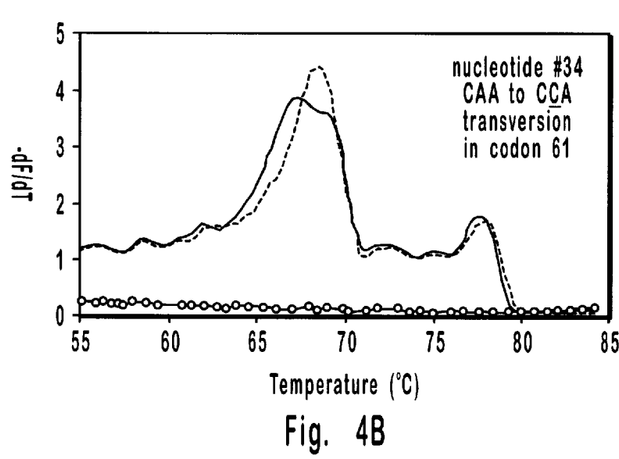
FIG. 4B is a graph illustrating the detection of heterozygous N-RAS codon 61 CAA→CCA transversion. The dashed line indicates the wild-type sequence. The solid line indicates the heterozygous samples. The line with circles indicates the "$H_2O$" control.

Referring to FIG. 4B, the results of the detection of heterozygous N-RAS codon 61 CAA→CCA transversion are illustrated. An anomalous melting profile with an additional melting peak (Tm~67° C.) distinct from the wild-type peak (Tm~69° C.) is observed. The wild-type peak in this illustration is represented as a "shoulder" rather than a distinct melting peak. The "$H_2O$" control shows fluorescence at levels below background.

Figure 4C:
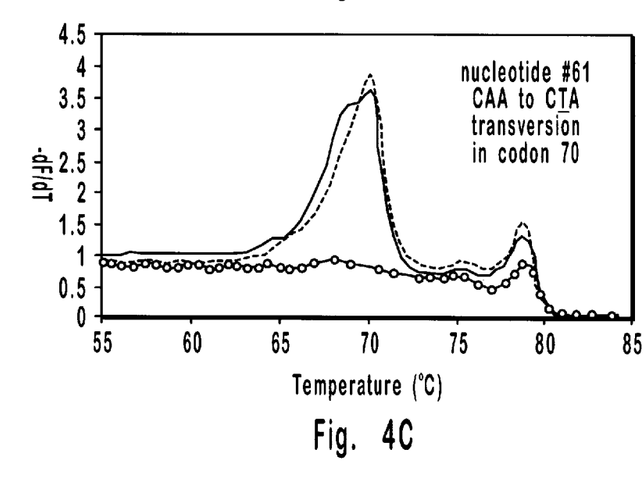
FIG. 4C is a graph illustrating the detection of heterozygous N-RAS codon 70 CAA→CTA transversion. The dashed line indicates the wild-type sequence. The solid line indicates the heterozygous samples. The line with circles indicates the "$H_2O$" control.

Referring to FIG. 4C, the detection of heterozygous N-RAS codon 70 CAA→CTA transversion is illustrated. An anomalous melting profile for the artificial heterozygous mutant with a prominent melting "shoulder" (Tm~68° C.) is distinguishable from the wild-type sample that exhibits a single peak (Tm~70° C.). The "$H_2O$" control shows fluorescence at levels below background.

Figure 4D:
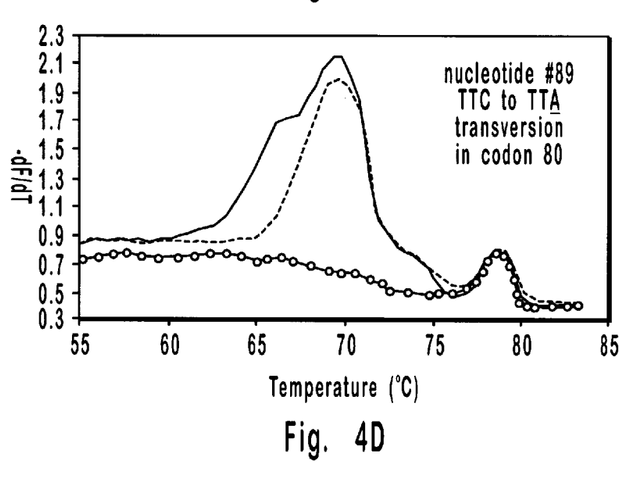
FIG. 4D is a graph illustrating the detection of heterozygous N-RAS codon 80 TTC→TTA transversion. The dashed line indicates the wild-type sequence. The solid line indicates the heterozygous sample. The line with circles indicates the "$H_2O$" control.

Referring to FIG. 4D, the detection of heterozygous N-RAS codon 80 TTC→TTA transversion. An anomalous melting profile for the artificial heterozygous mutant with a prominent melting "shoulder" (Tm~66° C.) is distinguishable from the wild-type sample that exhibits a single peak (Tm~70° C.). The "$H_2O$" control shows fluorescence at levels below background.

Example 9
Mutational Scanning by Slow Temperature Ramping and Chemical Denaturation Analysis of Homozygous N-RAS Codon 61 Mutant DNA The 9 possible single base substitutions in codon 61 of N-RAS were analyzed using the method of the present invention. Referring to FIG. 5, mutational scanning by slow temperature ramping analysis and chemical denaturation of GC-clamped N-RAS codon 61 amplicons revealed Tm shifts in the mutant PCR products that were predicted by the inherent stabilities of the base pair substitutions when compared with that of the wild-type sequence. Thus, while some mutant sequences consistently showed higher Tms than the wild-type sequence, 3 showed consistently lower Tms. Six homozygous mutant sequences yielded Tms indistinguishable from that of the wild-type sequence.

Referring to FIG. 5A, the analysis of the homozygous CAA→AAA transversion exhibits a single melting peak with a lower Tm (~68° C.) than the wild-type sample (Tm ~70° C.). The "$H_2O$" control shows fluorescence at levels below background.

Referring to FIG. 5B, the homozygous CAA→CTA transition exhibits a single melting peak with an indistinguishable Tm (~70° C.) from that of the wild-type sample (Tm~70° C.). The line with circles represents the no template or "$H_2O$" control.

Referring to FIG. 5C, the homozygous CAA→CAC transversion exhibits a higher Tm (~71° C.) than the wild-type sample (Tm~70° C.). The "$H_2O$" control shows fluorescence at levels below background.

In conclusion, a method for determining whether a DNA sequence is identical to a wild-type sequence is presented. A DNA segment of interest is amplified using primers to which a GC-clamp is attached to its 5' end. The GC-clamped DNA segment has two melting domains, a higher domain associated with the GC-clamp and a lower domain associated with the DNA sample. A fluorescent doubled stranded DNA binding dye is included in the amplification reaction. The reaction products are mixed with a denaturant and heated. Fluorescence is monitored to determine the melting temperature of the DNA sample. The melting temperature of the DNA sample is compared to the melting point of the wild-type sequence. A difference in melting temperatures of the DNA sequence and the wild-type sequence indicates an alteration in the DNA sequence. In a presently preferred embodiment, homozygous mutations may also be detected by combining approximately equal parts of the DNA sample with approximately equal parts of the wild-type sequence to create a heteroduplex. This is subjected to thermal amplification including a double stranded DNA binding dye, and the products are mixed with a denaturant and heated while monitoring fluorescence to determine the melting point of the heteroduplex. A difference in melting temperatures of the heteroduplex and the wild-type sequence indicates an alteration in the DNA sequence.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

I claim:

1. A method for determining whether a DNA sequence contains an alteration comprising:
   obtaining a DNA segment of interest, wherein the DNA segment of interest comprises one or more copies of the DNA sequence;
   attaching a GC-rich clamp to the DNA segment of interest;
   fluorescently labeling the DNA segment of interest;
   mixing the DNA segment of interest with a denaturant to create a mixture;
   heating the mixture of the fluorescently labeled DNA segment of interest and denaturant to melt the DNA segment of interest;
   monitoring fluorescence to obtain a melting temperature of the DNA segment of interest; and
   comparing the melting temperature of the DNA segment of interest with a melting temperature of a wild-type sequence, wherein a melting temperature for the DNA segment of interest that is different from the melting temperature for the wild-type sequence indicates an alteration in the DNA sequence.

2. The method of claim 1, further comprising the step of amplifying the DNA segment of interest.

3. The method of claim 1, wherein the denaturant is urea.

4. The method of claim 3, wherein the urea is at a concentration of about 13.3 M.

5. The method of claim 1, wherein the mixture is heated from about 33° C. to about 95° C.

6. The method of claim 1, wherein the mixture is heated at a rate from about 0.01° C. per second to about 0.1° C. per second.

7. The method of claim 6, wherein the mixture is heated at a rate of about 0.02° C. per second.

8. The method of claim 1, wherein the fluorescent labeling is a double stranded DNA binding dye.

9. The method of claim 8, wherein the double stranded DNA binding dye is SYBR® Green I, YO-PRO-I® or ethidium bromide.

10. The method of claim 1, wherein the GC-rich clamp is about 40 base pairs.

11. A method for determining whether a DNA sequence contains an alteration comprising:

obtaining a DNA segment of interest, wherein the DNA segment of interest comprises one or more copies of the DNA sequence;

combining the DNA segment of interest with an approximately equal amount of a wild-type sequence;

attaching a GC-rich clamp to the DNA segment of interest;

denaturing and annealing the DNA segment of interest and the wild-type sequence to create a heteroduplex;

fluorescently labeling the heteroduplex;

mixing the heteroduplex with a denaturant to create a mixture;

heating the mixture of the heteroduplex and the denaturant to melt the heteroduplex;

monitoring fluorescence to obtain a melting temperature of the heteroduplex; and comparing the melting temperature of the heteroduplex with a melting temperature of the wild-type sequence wherein a melting temperature for the heteroduplex that is different from the melting temperature for the wild-type sequence indicates an alteration in the DNA sequence.

12. The method of claim 11, further comprising the step of amplifying the DNA segment of interest.

13. The method of claim 11, wherein the denaturant is urea.

14. The method of claim 13, wherein the urea is at a concentration of about 13.3 M.

15. The method of claim 11, wherein the mixture is heated from about 33° C. to about 95° C.

16. The method of claim 11, wherein the mixture is heated at a rate from about 0.01° C. per second to about 0.1° C. per second.

17. The method of claim 16, wherein the mixture is heated at a rate of about 0.02° C. per second.

18. The method of claim 11, wherein the fluorescent label is a double stranded DNA binding dye.

19. The method of claim 18, wherein the double-stranded DNA binding dye is SYBR® Green I, YO-PRO-I® or ethidium bromide.

20. A method for determining whether a DNA sequence contains an alteration comprising:

obtaining a DNA segment of interest, wherein the DNA segment of interest comprises one or more copies of the DNA sequence;

combining the DNA segment of interest with an approximately equal amount of a wild-type DNA sequence;

attaching a GC-rich clamp to a primer;

amplifying the combination of the DNA segment of interest and the wild-type DNA sequence using the primer in the presence of a fluorescent double stranded DNA binding dye to create a fluorescently labeled heteroduplex;

mixing the heteroduplex with a denaturant to create a mixture;

heating the mixture of the heteroduplex and the denaturant;

monitoring fluorescence to obtain a melting temperature of the heteroduplex; and comparing the melting temperature of the heteroduplex with a melting temperature of the wild-type sequence wherein a melting temperature for the heteroduplex that is different from the melting temperature for the wild-type sequence indicates an alteration in the DNA sequence.

21. The method of claim 20, wherein the denaturant is urea.

22. The method of claim 21, wherein the urea is at a concentration of about 13.3 M.

23. The method of claim 22, wherein the mixture is heated from about 33° C. to about 95° C.

24. The method of claim 23, wherein the mixture is heated at a rate from about 0.01° C. per second to about 0.1° C. per second.

25. The method of claim 24, wherein the mixture is heated at a rate of about 0.02° C. per second.

26. The method of claim 20, wherein the double stranded DNA binding dye is SYBR® Green I, YO-PRO-I® or ethidium bromide.

* * * * *

```
                               SEQUENCE LISTING

<160> NUMBER OF SEQ ID NOS:   10

<210> SEQ ID NO 1
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 1
cctgtttgtt ggacataatg gatac                                              25

<210> SEQ ID NO 2
<211> LENGTH: 44
<212> TYPE: DNA
<213> ORGANISM: Artificial
<220> FEATURE:
<223> OTHER INFORMATION: Synthetic Oligonucleotide
<221> NAME/KEY: misc_feature
<222> LOCATION: (33)..(35)
<223> OTHER INFORMATION: n at position 33 is A, C, G, or T; n at
      position 34 is A, C, G, or T; and n at position 35 is A, C, G, or
      T

<400> SEQUENCE: 2
cctgtttgtt ggacatactg gatacagctg ganngaaga gtac                          44

<210> SEQ ID NO 3
<211> LENGTH: 55
<212> TYPE: DNA
<213> ORGANISM: Artificial
<220> FEATURE:
<223> OTHER INFORMATION: Synthetic Oligonucleotide

<400> SEQUENCE: 3
gatggcaaat acacagagga agccttcgcc tgtcctcatg taggtctctc atggc             55

<210> SEQ ID NO 4
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 4
gatggcaaat acacatagga agcc                                               24

<210> SEQ ID NO 5
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 5
cctgtttgtt ggacatactg                                                    20
```

```
<210> SEQ ID NO 6
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 6
cctgtttgtt ggacatactg                                              20

<210> SEQ ID NO 7
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 7
gatggcaaat acacagagga                                              20

<210> SEQ ID NO 8
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 8
cctgtttgtt ggaca                                                   15

<210> SEQ ID NO 9
<211> LENGTH: 13
<212> TYPE: DNA
<213> ORGANISM: Artificial
<220> FEATURE:
<223> OTHER INFORMATION: Synthetic Oligonucleotide

<400> SEQUENCE: 9
gatggcaaat aca                                                     13

<210> SEQ ID NO 10
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 10
cgcccgccgc gcccgcgcc cgtcccgccg ccccgcccg                          40
```